(12) United States Patent
Greer et al.

(10) Patent No.: US 7,384,430 B2
(45) Date of Patent: Jun. 10, 2008

(54) LOW CRYSTALLINE POLYMERIC MATERIAL FOR ORTHOPAEDIC IMPLANTS AND AN ASSOCIATED METHOD

(75) Inventors: Keith Greer, Fort Wayne, IN (US); Richard S. King, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 573 days.

(21) Appl. No.: 10/880,948

(22) Filed: Jun. 30, 2004

(65) Prior Publication Data
US 2006/0004168 A1 Jan. 5, 2006

(51) Int. Cl.
*A61F 2/28* (2006.01)
*C08J 3/28* (2006.01)

(52) U.S. Cl. ............... 623/11.11; 623/13.12; 623/18.11; 623/20.14; 623/20.11; 623/926; 522/161; 528/503; 422/1; 422/22; 264/485; 264/488

(58) Field of Classification Search ......... 623/13.12, 623/18.11, 20.14, 20.11, 926, 11.11; 528/503; 522/161; 264/346, 485, 488; 422/1, 22
See application file for complete search history.

(56) References Cited

U.S. PATENT DOCUMENTS

| | | |
|---|---|---|
| 2,948,666 A | 8/1960 | Lawton |
| 3,297,641 A | 1/1967 | Werber et al. |
| 3,352,818 A | 11/1967 | Meyer et al. |
| 3,646,155 A | 2/1972 | Scott ............ 260/827 |
| 3,671,477 A | 6/1972 | Nesbitt ............ 524/424 |
| 3,758,273 A | 9/1973 | Johnston et al. |
| 3,787,900 A | 1/1974 | McGee |
| 3,944,536 A | 3/1976 | Lupton et al. |
| 3,997,512 A | 12/1976 | Casey et al. |
| 4,055,862 A | 11/1977 | Farling |
| 4,138,382 A | 2/1979 | Polmanteer ............ 523/113 |
| 4,181,983 A | 1/1980 | Kulkarni |
| 4,195,366 A | 4/1980 | Jarcho et al. |
| 4,281,420 A | 8/1981 | Raab |
| 4,322,398 A | 3/1982 | Reiner et al. |
| 4,330,514 A | 5/1982 | Nagai et al. |
| 4,366,618 A | 1/1983 | Lakes |
| 4,373,217 A | 2/1983 | Draenert |
| 4,390,666 A | 6/1983 | Moriguchi ............ 525/194 |
| 4,452,973 A | 6/1984 | Casey et al. |
| 4,481,353 A | 11/1984 | Nyilas et al. |
| 4,483,333 A | 11/1984 | Wartman ............ 128/90 |
| 4,518,552 A | 5/1985 | Matsuo et al. ............ 264/126 |
| 4,539,374 A | 9/1985 | Fenton et al. ............ 525/240 |
| 4,563,489 A | 1/1986 | Urist |
| 4,578,384 A | 3/1986 | Hollinger |
| 4,582,656 A | 4/1986 | Hoffmann |
| 4,586,995 A | 5/1986 | Randall et al. |
| 4,637,931 A | 1/1987 | Schmitz |
| 4,655,769 A | 4/1987 | Zachariades |
| 4,668,527 A | 5/1987 | Fujita et al. ............ 427/35 |
| 4,743,493 A | 5/1988 | Sioshansi et al. |
| 4,747,990 A | 5/1988 | Gaussens et al. |
| 4,816,517 A | 3/1989 | Wilkus ............ 524/520 |
| 4,843,112 A | 6/1989 | Gerhart et al. |
| 4,876,049 A | 10/1989 | Aoyama et al. |
| 4,880,610 A | 11/1989 | Constantz |
| 4,888,369 A | 12/1989 | Moore, Jr. ............ 524/100 |
| 4,902,460 A | 2/1990 | Yagi ............ 264/83 |
| 4,944,974 A | 7/1990 | Zachariades |
| 5,001,206 A | 3/1991 | Bashir et al. |
| 5,014,494 A | 5/1991 | George |
| 5,024,670 A | 6/1991 | Smith et al. |
| 5,037,928 A | 8/1991 | Li et al. |
| 5,053,312 A | 10/1991 | Takeda |
| 5,084,051 A | 1/1992 | Tormala et al. |
| 5,085,861 A | 2/1992 | Gerhart et al. |
| 5,130,376 A | 7/1992 | Shih ............ 525/240 |
| 5,133,757 A | 7/1992 | Sioshansi et al. ............ 623/18 |
| 5,137,688 A | 8/1992 | DeRudder |
| 5,149,368 A | 9/1992 | Liu et al. |
| 5,153,039 A | 10/1992 | Porter et al. |
| 5,160,464 A | 11/1992 | Ward et al. |
| 5,160,472 A | 11/1992 | Zachariades |
| 5,180,394 A | 1/1993 | Davidson ............ 623/18 |
| 5,192,323 A | 3/1993 | Shetty et al. ............ 623/16 |
| 5,200,439 A | 4/1993 | Asanuma |

(Continued)

FOREIGN PATENT DOCUMENTS

| | | |
|---|---|---|
| BE | BE-A-1001574 | 12/1989 |
| DE | 196 10715 C1 | 6/1997 |
| EP | 0 169 259 | 7/1984 |
| EP | 0 373 800 A1 | 6/1990 |
| EP | 0 395 187 A2 | 10/1990 |
| EP | 0 505 634 | 9/1992 |
| EP | 0722973 A1 | 7/1996 |
| EP | 0729981 A1 | 9/1996 |
| EP | 0 737 481 A1 | 10/1996 |
| EP | 0 803 234 A1 | 10/1997 |

(Continued)

OTHER PUBLICATIONS

"Poly Two Carbon-Polyethylene Composite-A Carbon Fiber Reinforced Molded Ultra-High Molecular Weight Polyethylene", Technical Report, Zimmer (a Bristol-Myers Squibb Company), Warsaw (1977).

Atkinson, J.R. et al., "Silane cross-linked polyethylene for prosthetic applications. Part I. Certain physical and mechanical properties related to the nature of the material", Biomaterials, 4:267 (1983).

(Continued)

*Primary Examiner*—Fred Teskin
(74) *Attorney, Agent, or Firm*—Barnes & Thornburg LLP

(57) ABSTRACT

A component made from a crosslinked polymeric material, wherein the crosslinked polymeric material has a reduced crystallinity is described. An associated method for fabricating such a component is also described.

13 Claims, 8 Drawing Sheets

U.S. PATENT DOCUMENTS

| | | |
|---|---|---|
| 5,210,130 A | 5/1993 | Howard, Jr. |
| 5,236,563 A | 8/1993 | Loh ............................ 204/165 |
| 5,264,214 A | 11/1993 | Rhee et al. |
| 5,314,478 A | 5/1994 | Oka et al. |
| 5,356,998 A | 10/1994 | Hobes |
| 5,385,887 A | 1/1995 | Yim et al. |
| 5,407,623 A | 4/1995 | Zachariades et al. |
| 5,414,049 A | 5/1995 | Sun et al. ................. 525/333.7 |
| 5,439,949 A | 8/1995 | Lucas et al. |
| 5,449,745 A | 9/1995 | Sun et al. .................... 528/483 |
| 5,466,530 A | 11/1995 | England et al. |
| 5,478,906 A | 12/1995 | Howard, Jr. |
| 5,480,683 A | 1/1996 | Chabrol et al. |
| 5,492,697 A | 2/1996 | Boyan et al. |
| 5,508,319 A | 4/1996 | DeNicola .................... 526/352 |
| 5,515,590 A | 5/1996 | Pienkowski |
| 5,543,471 A | 8/1996 | Sun et al. |
| 5,549,698 A | 8/1996 | Averill et al. |
| 5,549,700 A | 8/1996 | Graham et al. |
| 5,577,368 A | 11/1996 | Hamilton et al. |
| 5,593,719 A | 1/1997 | Deamaley et al. .......... 427/2.26 |
| 5,607,518 A | 3/1997 | Hoffman et al. |
| 5,609,638 A | 3/1997 | Price et al. .................... 623/18 |
| 5,639,280 A | 6/1997 | Warner et al. |
| 5,645,594 A | 7/1997 | Devanathan et al. |
| 5,645,882 A | 7/1997 | Llanos ...................... 427/2.24 |
| 5,650,485 A | 7/1997 | Sun et al. |
| 5,674,293 A | 10/1997 | Armini et al. ................. 623/16 |
| 5,684,124 A | 11/1997 | Howard, Jr. et al. |
| 5,702,448 A | 12/1997 | Buechel et al. ............... 623/16 |
| 5,702,456 A | 12/1997 | Pienkowski .................. 623/18 |
| 5,709,020 A | 1/1998 | Pienkowski et al. |
| 5,728,748 A | 3/1998 | Sun et al. |
| 5,753,182 A | 5/1998 | Higgins |
| 5,876,453 A | 3/1999 | Beaty ........................... 623/16 |
| 5,879,388 A | 3/1999 | Pienkowski et al. .......... 623/18 |
| 5,879,400 A | 3/1999 | Merrill et al. ................. 623/22 |
| 5,879,407 A | 3/1999 | Waggener ..................... 623/22 |
| 5,947,893 A | 9/1999 | Agrawal et al. |
| 6,005,053 A | 12/1999 | Parikh et al. |
| 6,017,975 A | 1/2000 | Saum et al. |
| 6,027,742 A | 2/2000 | Lee et al. |
| 6,087,553 A | 7/2000 | Cohen et al. |
| 6,136,029 A | 10/2000 | Johnson et al. |
| 6,139,322 A | 10/2000 | Liu |
| 6,139,585 A | 10/2000 | Li |
| 6,143,232 A | 11/2000 | Rohr |
| 6,162,225 A | 12/2000 | Gertzman et al. |
| 6,168,626 B1 | 1/2001 | Hyon et al. |
| 6,228,900 B1 | 5/2001 | Shen et al. |
| 6,242,507 B1 | 6/2001 | Saum et al. |
| 6,245,276 B1 | 6/2001 | McNulty et al. |
| 6,281,262 B1 | 8/2001 | Shikinami |
| 6,281,264 B1 | 8/2001 | Salovey et al. |
| 6,296,667 B1 | 10/2001 | Johnson et al. |
| 6,302,913 B1 | 10/2001 | Ripamonti et al. |
| 6,316,158 B1 | 11/2001 | Saum et al. |
| 6,331,312 B1 | 12/2001 | Lee et al. |
| 6,376,573 B1 | 4/2002 | White et al. |
| 6,464,926 B1 | 10/2002 | Merrill et al. |
| 6,626,324 B1 | 9/2003 | Boyd |
| 2001/0027345 A1 | 10/2001 | Merrill et al. |
| 2002/0006428 A1 | 1/2002 | Mahmood et al. |
| 2007/0191504 A1* | 8/2007 | Muratoglu .................. 522/161 |

FOREIGN PATENT DOCUMENTS

| | | |
|---|---|---|
| EP | 0 963 824 A2 | 12/1999 |
| EP | 0 963 824 A3 | 9/2001 |
| EP | 1 208 958 | 5/2002 |
| EP | 1 277 450 A2 | 1/2003 |
| JP | 58-157830 A | 9/1983 |
| JP | A-59 168 050 | 9/1984 |
| JP | A-62 243 634 | 1/1987 |
| JP | 04-198242 | 7/1992 |
| JP | A-04 185651 | 7/1992 |
| JP | 09 12 22 22 | 5/1997 |
| WO | WO 93/10953 | 11/1991 |
| WO | WO 95/21212 | 8/1995 |
| WO | WO 96/09330 | 3/1996 |
| WO | WO 97/29793 | 8/1997 |
| WO | WO 98/01085 | 1/1998 |
| WO | WO 98/14223 | 4/1998 |
| WO | WO 98/29145 | 7/1998 |

OTHER PUBLICATIONS

Atkinson, J.R. et al., "Silane cross-linked polyethylene for prosthetic applications. Part II. Creep and wear behavior and a preliminary moulding test", Biomaterials, 5:326 (1984).

Bartel, D.L. et al., "The Effect of Comformity, Thickness, and Material on Stresses In Ultra-High Molecular Weight Components for Total Hip Replacement", J. Bone & Joint Surgery, 68-A(7):1041 (1986).

Bhateja, S.K., "Radiation-Induced Crystallinity Changes In Pressure-Crystallized Ultra-High Molecular Weight Polyethylene", J. Macromol. Sci. Phys., B22(1): 159 (1983).

Bhateja, S.K. et al., "Radiation-Induced Crystallinity Changes in Linear Polyethylene", J. Polym. Sci. Polym. Phys. Ed., 21: 523 (1983).

Bhateja, S.K. et al., "Radiation-Induced Crystallinity Changes in Polyethylene Blends", J. Mater. Sci., 20: 2839 (1985).

Birkinshaw, C. et al., "The Melting Behavior of Irradiated Polymers", Thermochimica Acta, 117: 365 (1987).

Bloebaum, R.D. et al., "Investigation of Early Surface Delamination Observed in Retrieved Heat-Pressed Tibial Inserts", Clin. Orthop., 269: 120 (1991).

Bremmer, T. et al., "Peroxide Modification of Linear Low-Density Polyethylene: A Comparison of Dialkyl Peroxides", J. Appl. Polym. Sci., 49 : 785 (1993).

Brown, K. J. et al., "The Wear of Ultra-High Molecular Weight Polyethylene with Reference to Its Use in Prostheses", Plastics in Medicine & Surgery Plastics & Rubber Institute, London, 2.1 (1975).

Chen, C.J. et al., "Radiation-Induced crosslinking: II. Effect on the crystalline and amorphous densities of polyethylene", Coll. & Polym. Sci.,269: 469 (1991).

Chen, Y.L. et al., "Photocrosslinking of Polyethylene I. Photoinitiators, Crosslinking Agent, and Reaction Kinetics", J. Polym. Sci., Part A: Polym. Chem. 27: 4051 (1989).

Chen, Y.L. et al., "Photocrosslinking of Polyethylene. II. Properties of Photocrosslinked Polyethylene", J. Polym. Sci., Part A; Polym. Chem., 27: 4077 (1989).

Connelly, G.M. et al., "Fatigue Crack Propagation Behavior of Ultrahigh Molecular Weight Polyethylene", J. Orthop. Res., 2: 119 (1984).

deBoer, A.P. et al., "Polyethylene Networks Crosslinked in Solution: Preparation, Elastic Behavior, and Oriented Crystallization. I. Crosslinking In Solution", J. Polym. Sci., Polym. Phys. Ed., 14: 187 (1976).

deBoer, J. et al., "Crosslinking of Ultra-High Molecular Weight Polyethylene in the Melt by Means of 2,5-dimethyl-2,5-bis (tert-butyldioxy)-3-hexyne", Makromol. Chem. Rapid Commun., 2: 749 (1981).

deBoer, J. et al., "Crosslinking of Ultra-High Molecular Weight Polyethylene in the Melt by Means of 2,5-dimethyl-2,5-bis (tert-butyldioxy)-3-hexyne: 2. Crystallization Behavior and Mechanical Properties", Polymer, 23: 1944 (1982).

deBoer, J. et al., "Crosslinking of Ultra-High Molecular Weight Polyethylene in the Oriented State with Dicumylperoxide", Polymer, 25: 513 (1984).

Dijkstra, D.J. et al., "Cross-linking of ultra-high molecular weight polyethylene in the melt by means of electron beam irradiation", Polymer, 30: 866 (1989).

Ding Z.Y. et al., "Model Filled Polymers. VI. Determination of the Crosslink Density of Polymeric Beads by Swelling," J. Polym. Sci., Part B: Poly. Phys., 29: 1035 (1991).

Eyerer, P. et al., "Property changes of UHMW polyethylene hip cup endoprostheses during implantation", J. Biomed. Materials Res., 18: 1137 (1984).

Eyerer, P., "Polyethylene", Concise Encyclopedia of Medical and Dental Implant Materials, Pergamon Press, Oxford, 271 (1990).

Ferris, B.D., "A quantitiative study of the tissue reaction and its relationship to debris production from a joint implant", J. Exp. Path., 71: 367 (1990).

Gielenz G. et al., "Crystalline and supermolecular structures in linear polyethylene irradiated with fast electrons", Colloid & Polymer Sci., 260: 742 (1982).

Grobbelaar, C.J. et al., "The Radiaion improvement of Polyethylene Prosthesis", J. Bone & Joint Surgery, 60-B(3): 370-374 (1978).

Goodman, S. et al., "Polyethylene wear in knee arthroplasty", Acta Orthop. Scand., 63(3): 358 (1992).

Grood, E.S. et al., "Analysis of retrieved implants: Crystallinity changes in ultrahigh molecular weight polyethylene", J. Biomedical Materials Res., 16: 399 (1982).

Huang, D.D. et al., "Cyclic Fatigue Behaviors of UHMWPE and Enhanced UHMWPE", Trans. 38th Ann. Mtg., Orthop. Res. Soc., 403 (1992).

Kamel, I. et al., "A Model for Radiation-Induced Changes in Ultrahigh-Molecular-Weight-Polyethylene", J. Polym. Sci., Polym. Phys. Ed., 23:2407 (1985).

Kampouris, E.M. et al., "Benzyl Peroxide as a Crosslinking Agent for Polyethylene", J. Appl. Polym. Sci., 34: 1209 (1987).

Kao, Y.H., "Crystallinity in chemically crosslinked low density polyethylenes: 1 Structural and fusion studies", Polymer, 27: 1669 (1986).

Katq, K. et al., "Structural Changes and Melting Behavior of γ-Irradiated Polyethylene", Japanese J. Appl. Phys., 20: 691 (1981).

Kunert, K.A. et al., "Structural investigation of chemically crosslinked low density polyethylene", Polymer, 22: 1355 (1981).

Kurth, M. et al., "Effects of Radiation Sterilization on UHMW-Polyethylene", Trans. Third World Biomaterials Congress, 589 (1988).

Landy, M.M. et al., "Wear of Ultra-high-molecular-weight Polyethylene Components of 90 Retrieved Knee Prostheses", J. Arthroplasty, Supplement, 3: S73 (1988).

Lem, K. et al., "Rheological Properties of Polyethylenes Modified with Dicumyl Peroxide", J. Appl. Polym. Sci., 27: 1367 (1982).

Li, S. et al., "Characterization and Description of an Enhanced Ultra High Molecular Weight Polyethylene for Orthopaedic Bearing Surfaces", Trans. 16th Ann. Soc. Biomaterials Meeting, Charleston, SC, 190 (1990).

Manley, T.R. et al., "The effects of varying peroxide concentration in crosslinked linear polyethylene", Polymer, 12:176 (1971).

McKellop, H. et al., "Friction, Lubrication and Wear of Polyethylene Metal and Polyethylene/Ceramic Hip Prostheses on a Joint Simulator", Fourth World Biomaterials Congress, Berlin, April., 118 (1992).

Minkova, L., "DSC of γ-irradiated ultra-high molecular weight polyethylene and high density polyethylene of normal molecular weight", Colloid & Polymer Sci., 266: 6 (1988).

Minkova, L. et al., "Blends of normal high density and ultra-high molecular weight polyethylene, γ-irradiated at a low dose", Colloid & Polymer Sci., 268: 1018 (1990).

Nagy, E.V. et al., "A Fourier transform infrared technique for the evaluation of polyethylene orthopaedic bearing materials", Trans. 16th Ann. Soc. For Biomaterials Meeting, Charleston, SC 109 (1990).

Narkis, M. et al., "Structure and Tensile Behavior of Irradiation-and Peroxide-Crosslinked Polyethylene", J. Macromol. Sci.-Phys., B26(1): 37 (1987).

Nusbaum, H. J. et al., "The Effects of Radiation Sterilization on the Properties of Ultrahigh Molecular Weight Polyethylene", J. Biomed. Materials Res., 13: 557 (1979).

Oonishi, H. et al., "Improvement of Polyethylene by Irradiation in Artificial Joints", Radiat, Phys. Chem., 39: 495 (1992).

Oonishi, H. et al., "In Vivo and In Vitro Wear Behavior on Weightbearing Surfaces of Polyethylene Sockets Improved by Irradiation in Total Hip Prostheses", Surface Modification Technologies V, 101-115 (1992), Sudarsahn T.S. et al., ed. The Institute of Materials.

Painter, P.C., et al., "The Theory of Vibrational Spectroscopy and its Application to Polymeric Materials", Ed. John Wiley & Sons, New York, U.S.A., (1982).

Paul, J. P., "Forces Transmitted by Joints in the Human Body", Proc. Instn. Mech. Engrs. 181, Part 3J, Paper 8 (1966).

Qu, B.J. et al., "Photocross-linking of Low Density Polyethylene. I Kinetics and Reaction Parameters", J. Appl. Polym. Sci., 48: 701 (1993).

Qu, B.J. et al., "Photocross-linking of Low Density Polyethylene. II Structure and Morphology", J. Appl. Polym. Sci., 48: 711 (1993).

Rimnac, C.M. et al., "Chemical and Mechanical Degradation of UHMWPE: Report of the Development of an In vitro Test", J. Appl. Biomaterials, 5:17 (1994).

Rimnac, C.M. et al., "Observations of Surface Damage and Degradation on Retrieved PCA Knee Implants", Trans. 38th Ann. Orthopaedic Res. Society, Washington, D.C., 330 (1992).

Rimnac, C.M. et al., "Post-Irradiation Aging of Ultra-High Molecular Weight Polyethylene", J. Bone & Joint Surgery, 76-A(7): 1052 (1994).

Roe, R. et al., "Effect of radiation sterilization and aging on ultrahigh molecular weight polyethylene", J. Biomed. Mat. Res., 15: 209 (1981).

Rose, R.M. et al., "On the True Wear Rate of Ultra-High Molecular Weight Polyethylene in the Total Hip Prosthesis", J. Bone & Joint Surgery, 62A(4): 537(1980).

Rose, R.M. et al., "Exploratory Investigations in the Structure Dependence of the Wear Resistance of Polyethylene", Wear, 77:89 (1982).

Rostoker, W. et al., "The Appearances of Wear on Polyethylene—A Comparison of in vivo and in vitro Wear Surfaces", J. Biomed. Materials Res., 12:317 (1978).

Seedhom, B.B. et al., "Wear of Solid Phase Formed High Density Polyethylene in Relation to the Life of Artificial Hips and Knees", Wear, 24: 35 (1973).

Shen, C. et al., "The Friction and Wear Behavior of Irradiated Very High Molecular Weight Polyethylene", Wear, 30:349 (1974).

Shinde, A. et al., "Irradiation of Ultrahigh-Molecular-Weight Polyethylene", J. Polym. Sci., Polym. Phys. Ed., 23: 1681 (1985).

Spruiell, J.E. et al., "Methods of Experimental Physics", L. Marton & C. Marton, Eds., vol. 16, Part B Academic Press, New York (1980).

Streicher, R.M., "Ionizing irradiation for sterilization and modification of high molecular weight polyethylenes" Plastics & Rubber Processing & Applications, 10: 221 (1988).

Streicher, R.M., "Investigation on Sterilization and Modification of High Molecular Weight Polyethylenes by Ionizing Irradiation", Beta-gamma, 1/89:34-43.

Swanson, S.A.V. et al., "Chapter 3, Friction, Lubrication and Wear", The Scientific Basis of Joint Replacement, Pittman Medical Publishing Co., Ltd. (1977).

Wang, X. et al., "Melting of Ultrahigh Molecular Weight Polyethylene", J. App. Polymer Sci., 34:593 (1987).

Wright, T.M. et al., "The effect of carbon fiber reinforcement on contact area, contact pressure, and time-dependent deformation in polyethylene tibial components", J. Biomed. Materials Res., 15:719 (1981).

Zachariades, A.E., "A New Class of UHMWPE Orthopaedic Prosthetic Devices with Enhanced Mechanical Properties", Trans. Fourth World Biomaterials Congress, Berlin 623 (1992).

Zhao, Y. et al., "Effect of Irradiation on Crystallinity and Mechanical Properties of Ultrahigh Molecular Weight Polyethylene", J. Appl. Polym. Sci., 50:1797 (1993).

"News You Can Use", vol. II, No. 2 (May 1996).

"For the Tough Jobs: 1900 UHMW Polymer", Himont, Inc. (1988).

"Abrasion-Resistant 1900 UHMW Polymer", Hercules, Inc. (1979).

"Technical Information: 1900 Ultrahigh Molecular Weight Polymer, General Information and Applications", Bulletin JPE-101A, Hercules, U.S.A., Inc., (1989).

"Technical Information: 1900 Ultrahigh Molecular Weight Polymer, Nuclear Radiation Effects", Bulletin HPE-111, Himont U.S.A., Inc. (1985).

"Technical Information: 1900 Ultrahigh Molecular Weight Polymer, Effect of Polymer Modification", Bulletin HPE-116, Himont U.S. A., Inc. (1987).

"Ultra-High Molecular Weight Polyethylene as Biomaterial In Orthopaedic Surgery", Hogrefe & Huber Publishers.

Appleby, R.W. et al., "Post-gamma irradiation cross-linking of polyethylene tape by acetylene treatment", J. Material Sci., 29: 227-231 (1994).

Higgins, J.C. et al., "Evaluation of Free Radical Reduction Treatments for UHMWPE", Proceedings of the 42$^{nd}$ Annual Mtg., Orthopaedic Res. Soc., Feb. 19-22:485(1996).

Jasty, M. et al., "Marked Improvement in the Wear Resistance of a New Form of UHMPWE in a Physiologic Hip Simulator", Trans. 43$^{rd}$ Ann. Mtg., Orthopaedic Research Soc., San Francisco, CA, Feb. 9-13:785(1997).

Jasty, M. et al., "Marked Improvement in the Wear Resistance of a New Form of UHMPWE in a Physiologic Hip Simulator", Trans. Soc. Biomaterials, vol. XX, p. 71, 23$^{rd}$ Ann. Mtg. Soc. for Biomaterials. New Orleans, Louisana, U.S.A., Apr. 30-May 4:157 (1997).

Streicher, Influence of Ionizing Irradiation in Air and Nitrogen for Sterilization of Surgical Grade Polyethylene for Implants, Radiat. Phys. Chem., vol. 31, Nos. 4-6: 693-698 (1988).

Pleiss et al., "The Improvement of Polyethylene Prostheses Through Radiation Crosslinking", Radiat . . . Phys. Chem., 9: 647-652 (1977).

Streicher, "The Behavior of UHMW-PE when Subjected to Sterilization by Ionizing Radiation", Ultra-High Molecular Weight Polyethylene as Biomaterial in Orthopedic Surgery, 66-73 (1990).

Saunders, C. et al., "Radiation Effects on Microorganisms and Polymers for Medical Products", Medical Device & Diagnostic Industry, 222:89-22 (1993).

Kang et al., "The Radiation Chemistry of Polyethylene IX. Temperature Coefficient of Cross-linking and Other Effects", J. Amer. Chem. Society, 89(9): 1980-1986 (1967).

Rose et al., "Radiation Sterilization and the Wear Rate of Polyethylene", J. Orthopaedic Res. Society, 2(4): 393-400 (1984).

Oonishi, H. et al., "Super Low Wear Cross-Linked UHMWPE by Heavy High-Dose Gamma Radiation", WPOA 2$^{nd}$ Congress of Hip Section, 61 (1996).

Jahan et al., "Combined chemical and mechanical effects on free radicals in UHMWPE joints during implantation", J. Biomed. Material Res., 25: 1005-1016 (1991).

"Standard Practice for Dosimetry in an Electron Bean Facility for Radiation Processing at Energies Between 300 keV and 25 keV", Am. Soc. for Testing & Materials, Designation: E1649-94, 870-888 (1995).

Oonishi, H. et al., "The Low Wear of Cross-Linked Polyethylene Socket in Total Hip Prostheses", Encyclopedic Handbook of Biomaterials & Bioengineering, vol. 2, Marcel Dekker, Inc., 1853-1868 (1995).

Atkinson, J. et al., "The nature of silane cross-linked HDPE is discussed. Creep and wear tests indicate its potential as a possible replacement for high molecular weight polyethylene in prostheses", Polymers in Medicine and Surgery, Conf. Held by Plastics and Rubber Institute and Biological Engineering Soc., UK. Sep, P4/1-P4/9 (1986).

Jones, W. et al., Effect of γ Irradiation on the Friction and Wear of Ultrahigh Molecular Weight Polyethylene, Wear 70: 77-92 (1981).

Gent, A. et al., "Elastic Behavior, Birefringence, and Swelling of Amorphous Polyethylene Networks", J. Polymer Sci. 5: 47-60 (1967).

Zoepfl, F. et al., "Differential Scanning Calorimetry Studies of Irradiated Polyethylene: I. Melting Temperatures and Fusion Endotherms", J. Polymer Sci. Polym. Chem. Ed., 22: 2017-2032 (1984).

Zoepfl, F. et al., "Differential Scanning Calorimetry Studies of Irradiated Polyethylene: II. The Effect of Oxygen", J. Polymer Sci. Polym. Chem. Ed., 22: 2032-2045 (1984).

Mandelkern, L. et al., "Fusion of Polymer Networks Formed from Linear Polyethylene: Effect of Intermolecular Order", contribution from the General Electric Research Laboratory and from the Polymer Structure Section, National Bureau of Standards 82: 46-53 (1960).

Muratoglu, O.K. et al., "A Comparison of 5 Different Types of Highly Crosslinked UHMWPES: Physical Properties and Wear Behavior", 45$^{th}$ Annual Meeting, Orthopaedic Research Society, Anaheim, CA, Feb. 1-4, 77 (1999).

Muratoglu, O.K. et al., "A Novel Method of Crosslinking UHMWPE to Improve Wear With Little or No Sacrifice on Mechanical Properties", 45$^{th}$ Annual Meeting, Orthopaedic Research Society, Anaheim, CA, Feb. 1-4, 829 (1999).

Muratoglu, O.K. et al., "Electron Beam Cross Linking of UHMWPE At Room Remperature, A Candidate Bearing Material for Total Joint Arthroplasty", 23rd Annual Meeting of the Society for Biomaterials, New Orleans, Louisana, Apr. 30-May 4, 74 (1997).

Matsubara, K et al., "The Wear Properties of High-Density Polyethylene Irradiated by Gamma Rays", Wear 10: 214 (1967).

McKellop, H. et al., "Increased Wear of UHMW Polyethylene After Gamma Radiation Sterilization", Trans. 26$^{th}$ Ann. ORS, Atlanta, Georgia, Feb. 5-7, 1980.

McKellop, H., "The Effect of Radiation and Ethylene Oxide Sterilization on the Wear of UHMW Polyethylene", 7$^{th}$ European Conference on Biomaterials, Sep. 8-11, 1987.

Shen, F-S. et al., "Irradiation of Chemically Crosslinked Ultrahigh Molecular Weight Polyethylene", J. Polymer Sci.: Part B: Polymer Phys. 34: 1063-1077 (1996).

Oka, M. et al., "Wear-Resistant Properties of Newly Improved UHMWPE", Trans. Fifth World Biomaterials Congress, Toronto, Canada 520, (May 29-Jun. 2, 1996).

Bellare, A. et al., "Deformation, Morphology and Wear Behavior of Polyethylene", Trans. 23$^{rd}$ Ann. Mtg., Soc. Biomaterials, New Orleans, Louisiana, 75 (Apr. 30-May 4, 1997).

Clarke, I.C. et al., "Simulator Wear Study of High-Dose Gamma-Irradiated UHMWPE Cups", Trans. 23$^{rd}$. Ann. Mtg., Soc. Biomaterials, New Orleans, LA, 71, (Apr. 30-May 4, 1997).

Taylor, G. et al., "Stability of $N_2$ Packaged Gamma Irradiated UHMWPE", Trans. 23$^{rd}$ Ann. Mtg., Soc. Biomaterials, New Orleans, LA, 421, (Apr. 30-May 4, 1997).

Taylor, G. et al., "Stability of $N_2$ Packaged Gamma Irradiated UHMWPE", Trans. 43$^{rd}$ Ann. Mtg., Orthopaedic Res. Soc., San Francisco, California, 776 (Feb. 9-13, 1997).

McKellop, H. et al., "The Effect of Sterilization Method, Calcium Stearate and Molecular Weight on Wear of UHMWPE Acetabular Cups", Trans. 23$^{rd}$ Ann. Mtg., Soc. Biomaterials, New Orleans, LA, 43 (Apr. 30-May 4, 1997).

McKellop, H. et al., "Effect of Sterilization Method on the Wear Rate of UHMW Polyethylene Acetabular Cups in a Hip Simulator", Trans. 43$^{rd}$ Ann. Mtg., Orthopaedic Res. Soc. San Francisco, CA, 7, 94-16 Feb. 9-13, 1997.

McKellop, H. et al., "Wear of UHMWPE Acetabular Cups After Gamma Sterilization in Nitrogen, Thermal Stabilization and Artificial Aging", Trans. 23$^{rd}$ Ann. Mtg., Soc. Biomaterials, New Orleans, LA, Apr. 30-May 4, 45 (1997).

Wang, A. et al., "Effect of Radiation Dosage on the Wear of Stabilized UHMWPE Evaluated by Hip and Knee Joint Simulators", Trans. 23$^{rd}$ Ann. Mtg., Soc. Biomaterials, New Orleans, LA, 394 (Apr. 30-May 4, 1997).

Wang, A. et al., "Wear Mechanisms and Wear Testing of Ultra-High Molecular Weight Polyethylene in Total Joint Replacements", Hand-Out for Polyethylene Wear in Orthopaedic Implants Workshop, Trans. 23$^{rd}$ Ann. Mtg., Soc. Biomaterials, New Orleans, LA (Apr. 30-May 4, 1997).

Yu, Y.J. et al., "Oxidation of UHMWPE Acetabular Cups After Sterilization and Wear Testing in a Hip Joint Simulator", Trans. 43$^{rd}$ Ann. Mtg., Orthopaedic Res. Soc. San Francisco, CA, 778 (Feb. 9-13, 1997).

Roe, R. et al., "Effect of Radiation Sterilization and Aging on Ultrahigh Molecular Weight Polyethylene", Journal of Biomedical Materials Research, 15:209-230 (1981).

Li, S. et al., "Chemical Degradation of Polyethylene in Hip and Knee Replacements", 38th Ann. Mtg., Orthopaedic Research Society, Washington, D.C., 41, (Feb. 7-20, 1992).

Kurtz, S.M. et al., "Post-Irradiation Aging and The Stresses in UHMWPE Components for Total Joint Replacement", 40th Ann. Mtg., Orthopaedic Research Society, New Orleans, LA, 584, (Feb. 21-24, 1994).

Lancaster et al., "Friction and Wear", in Jenkins (ed): Polymer Science, 959, 1045, North Holland Publishing Company (1972).

McKellop, H. et al., "Accelerated Aging of Irradiated UHMW Polyethylene for Wear Evaluations", 42nd Annual Meeting, Orthopaedic Research Society, Atlanta, Georgia, 483, (Feb. 19-22, 1996).

Blunn, G.W. et al., "The Effect of Oxidation on the Wear of Untreated and Stabilized UHMWPE", 42nd Annual Meeting, Orthopaedic Research Society, Atlanta, Georgia, 482, (Feb. 19-22, 1996).

"Duration™ Stabilized UHMWPE: an UHMWPE with Superior Wear and Oxidation Resistance; Technical Development and Scientific Evaluation", (Cover sheet and reference page).

Sun, D.C. et al., "The Origin of the White Band Observed in Direct Compression Molded UHMWPE Inserts", 20th Annual Meeting Society for Biomaterials, 121 (Apr. 5-9, 1994).

Sun, D.C. et al., "On the Origins of a Subsurface Oxidation Maximum and its Relationship to the Performance of UHMWPE Implants", 21st Annual Meeting, Society for Biochemicals, San Francisco, CA, 362: (Mar. 18-22, 1995).

Premnath, V. et al., "Melt Irradiated UHMWPE for Total Hip Replacement: Synthesis & Properties", 43rd Annual Meeting, Orthopedic Res. Soc., San Francisco, CA, 91-16, (Feb. 9-13, 1997).

Muratoglu, O.K. et al., "The Effect of Temperature on Radiation Crosslinking of UHMWPE for Use in Total Hip Arthroplasty", 46th Annual Meeting, Orthopaedic Res. Soc., Orlando, FL, 0547 (Mar. 12-15, 2000).

D.C. Sun, C. Stark, J.H. Dumbleton, "Development of an Accelerated Aging Method For Evaluation of Long-term Irradiation Effects on UHMPWE Implants", *Polymer Preprints*, vol. 35, No. 2, pp. 969-970, (1994).

A.F. Booth, "Industrial Sterilization Technologies: New and Old Trends Shape Manufacturer Choices", Medical Device & Diagnostic Industry, pp. 64-72, Feb. 1995.

B. Hinsch, "Sterilization Methods for Implants Made of UHMWPE", in Ultra-High Molecular Weight Polyethylene as Biomaterials in Orthopedic Surgery, Toronto: Hogrefe & Huber Publishers, pp. 63-65, (1991).

"Irradiation Effects on Polymers", edited by D.W. Clegg and A.A. Collyer, Elsevier Applied Science, London, (1991).

"Radiation Effects on Polymers", edited by R. L. Clough and S. W. Shalaby, ACS Symposium Series 475, (1991).

P. Eyerer, M. Kurth, H. A. McKellop and T. Mittimeier, "Characterization of UHMWPE hip cups run on joint stimulators", J. Biomedical Materials Research, vol. 21, pp. 275-291, (1987).

A. Wang, D.C. Sun, C.Stark, J.H. Dumbleton, Wear, pp. 181-183:241-249 (1995).

A. Wang, C. Stark, J.H. Dumbleton, "Role of cyclic plastic deformation in the wear of UHMWPE acetabular cups", Journal of Biomedical Materials Research, vol. 29, pp. 619-626, (1995).

A. Edidin et al., "Enhancement of multiaxial mechanical behavior by slot drawing of UHMWPE: a candidate biomaterial for total knee arthroplasty," 46th Annual Mtg., Orthopaedic. Res. Soc., Mar. 12-15, Orlando, FL (2000).

Watkins et al."Fractionation of High Density Polyethylene in Propane by Isothermal Pressure Profiling and Isobaric Temperature Profiling" J. Supercritical Fluids, 4:24-31 (1994).

Q. Qiu, Ph. D. et al., "Formation and Differentiation of Three-Dimensional Rat Marrow Stromal Cell Culture on Microcarriers in a Rotating-Wall Vessel", Tissue Engineering, vol. 4, No. 1, 1998.

Qing-Qing Qiu et al., "Fabrication, characterization and evaluation of bioceramic hollow microspheres used as microcarriers for 3-D bone tissue formation in rotating bioreactors", Biomaterials 20, p. 989-1001, 1999.

Robert Langer, "New Methods of Drug Delivery", Science, 249, Articles, p. 1527-1533. Sep. 28, 1990.

Larry L. Hench, "Bioactive Ceramics", Annals New York Academy of Sciences, p. 54-71.

Paul Ducheyne, "Stimulation of Biological Function with Bioactive Glass", MRS Bulletin, p. 43-49, Nov. 1998.

Q. Qiu, et al., "A novel bioactive, resorbable composite microsphere for bone tissue engineering and regeneration", Society for Biomaterials, Sixth World Biomaterials Congress Transactions, p. 433, 2000.

Mutsuhiro Maeda, et al., "Histological Study of Carboxymethyl-chitn/Hydroxyapatite Composite for Bone Repair", Society for Biomaterials, 27th Annual Meeting Transactions, p. 416, 2001.

S. M. Kurtz et al., "Advances in the processing, sterilization, and crosslinking of ultra-high molecular weight polyethylene for total joint arthroplasty", *Biomaterials*, XP002315568, vol. 20, No. 18, 1999, pp. 1659-1688.

European Search Report for European Application No. 05253571. 3-2107, Oct. 7, 2005, 3 pgs.

* cited by examiner

| Sample | Depth (μm) | Sample 1 | Sample 2 | Average | Standard Deviation | Depth (μm) | Sample 1 | Sample 2 | Average | Standard Deviation | Crystallinity Difference |
|---|---|---|---|---|---|---|---|---|---|---|---|
| CR-RT | 200 | 40.45 | 42.02 | 41.96 | 1.36 | 12700 | 43.49 | 46.59 | 44.83 | 1.64 | 2.87 |
| CR-RT | 600 | 40.84 | 41.66 | | | 12300 | 45.51 | 45.05 | | | |
| CR-RT | 1000 | 44.26 | 42.54 | | | 11900 | 42.27 | 46.08 | | | |
| CR-50 | 200 | 40.09 | 40.26 | 41.67 | 1.55 | 12700 | 45.14 | 45.71 | 44.42 | 1.69 | 2.75 |
| CR-50 | 600 | 40.76 | 42.41 | | | 12300 | 45.77 | 41.79 | | | |
| CR-50 | 1000 | 43.99 | 42.52 | | | 11900 | 45.29 | 42.83 | | | |
| CR-50-2 | 200 | 43.01 | 42.71 | 41.42 | 1.17 | 12700 | 44.68 | 44.65 | 43.13 | 2.00 | 1.72 |
| CR-50-2 | 600 | 41.15 | 40.65 | | | 12300 | 45.16 | 40.2 | | | |
| CR-50-2 | 1000 | 40.13 | 40.84 | | | 11900 | 42.34 | 41.76 | | | |
| CR-100 | 200 | 40.17 | 40.86 | 41.91 | 2.26 | 12700 | 47.17 | 47.14 | 46.49 | 0.53 | 4.58 |
| CR-100 | 600 | 40.48 | 40.32 | | | 12300 | 46.25 | 46.23 | | | |
| CR-100 | 1000 | 44.88 | 44.76 | | | 11900 | 45.89 | 46.25 | | | |
| CR-100-2 | 200 | 43.86 | 45.18 | 42.66 | 1.66 | 12700 | 46.82 | 44.59 | 44.80 | 1.20 | 2.14 |
| CR-100-2 | 600 | 40.92 | 40.95 | | | 12300 | 45.59 | 44.29 | | | |
| CR-100-2 | 1000 | 42.68 | 42.38 | | | 11900 | 43.93 | 43.58 | | | |
| CR-100-3 | 200 | 42.28 | 41.92 | 43.38 | 1.06 | 12300 | 43.94 | 45.68 | 44.89 | 1.36 | 1.51 |
| CR-100-3 | 600 | 43.86 | 43.87 | | | 11900 | 46.63 | 44.79 | | | |
| CR-100-3 | 1000 | 43.6 | 44.72 | | | 11500 | 45.46 | 42.81 | | | |
| CR-TWO | 200 | 42.98 | 41.24 | 41.84 | 1.45 | 12700 | 42.89 | 43.02 | 44.68 | 1.48 | 2.84 |
| CR-TWO | 600 | 42.83 | 42.99 | | | 11500 | 44.89 | 46.41 | | | |
| CR-TWO | 1000 | 39.27 | 41.74 | | | 11000 | 46.08 | 44.81 | | | |
| CR-OFF | 200 | 47.22 | 46.22 | 47.18 | 0.94 | 12700 | 47.99 | 47.45 | 47.70 | 0.58 | 0.52 |
| CR-OFF | 600 | 47.03 | 46.27 | | | 12300 | 47.13 | 48.58 | | | |
| CR-OFF | 1000 | 48.75 | 47.57 | | | 11900 | 47.94 | 47.09 | | | |

Fig. 7

LOW CRYSTALLINE POLYMERIC MATERIAL FOR ORTHOPAEDIC IMPLANTS AND AN ASSOCIATED METHOD

TECHNICAL FIELD

The present disclosure generally relates to low crystalline polymeric material and an associated method of treating a polymeric material. The present disclosure particularly relates to (i) a low crystalline polymeric material for use in orthopaedic devices for implantation in the body of an animal and (ii) a method of treating a polymeric material for use in orthopaedic devices for implantation in the body of an animal.

BACKGROUND

Implantable prosthetic devices typically include a component constructed from a polymeric material, such as polyethylene. For example, many implantable prosthetic devices include a bearing component, such as an acetabular bearing, a glenoid bearing, or a tibial bearing made from a polymeric material such as Ultra-High Molecular Weight Polyethylene (UHMWPE). UHMWPE is utilized in the construction of prosthetic bearing components due to its favorable mechanical and wear characteristics. Moreover, it has been determined that certain characteristics of polymeric materials, such as UHMWPE, may be enhanced by exposing the material to radiation. For example, exposing UHMWPE to predetermined doses of radiation crosslinks the UHMWPE and thereby increases its wear resistance. Accordingly, many prosthetic devices include a bearing component constructed of crosslinked UHMWPE in order to gain the aforementioned benefits.

However, the irradiation of polymeric materials, like UHMWPE, to increase their wear resistance can also cause the degradation of other mechanical characteristics of the material. For example, the mechanical characteristics which allow a polymer component to appropriately withstand high stress applications, such as those associated with locking rings and tabs, can deteriorate if the polymeric material is exposed to certain amounts of radiation. One approach to this problem is not to use highly crosslinked UHMWPE in high stress designs. For example, in some instances UHMWPE is only exposed to a reduced or low dose of radiation so that it will have adequate mechanical properties to withstand these high stress designs. Therefore, this UHMWPE will only be crosslinked to a low degree. However, a problem with this approach is that the wear rate of this low crosslinked polymeric material tends to be less than optimal. Therefore, a polymeric material and associated method for treating a polymeric material that results in it having an enhanced wear rate and other mechanical properties (e.g. the properties which allow the material to appropriately withstand high stress applications) is desirable.

SUMMARY

A method in accordance with an illustrative embodiment of the present disclosure includes one or more of the following features or combinations thereof:

In one embodiment the present disclosure provides a method for treating a polymeric material. The polymeric material can be consolidated into a work piece. For example, the work piece can be in the form of a rod, bar, sheet or molded component. Moreover, polymeric material which is porous or nonporous may be utilized. In another embodiment, the polymeric material can be utilized to fabricate a polymeric bearing component. For example, the polymeric material can be utilized to fabricate a polymeric bearing component of an implantable orthopaedic device, such as a knee, hip, shoulder, or elbow prostheses. Accordingly, the polymeric material can be any medical grade polymeric material which may be implanted into the body of an animal (e.g. the body of a human patient). An example of a polymeric material that can be treated with the method described herein is medical grade polyethylene such as polyethylene homopolymer, high density polyethylene, high molecular weight polyethylene, high density high molecular weight polyethylene, or any other type of polyethylene utilized in the construction of a prosthetic implant. A more specific example of such a polymer is medical grade ultra-high molecular weight polyethylene (UHMWPE).

In addition, the polymeric material utilized, for example, to fabricate a polymeric bearing component has a crystallinity. For example, initially the crystallinity of the polymeric material can be greater than about 50%, such as a semicrystalline polymeric material. In particular, the initial crystallinity of the polymeric material can be, for example, in the range of from about 50% to about 70%. Even more particular, the initial crystallinity of the polymeric material can be, for example, in the range of from about 50% to about 60%. The method can include changing the crystallinity of the polymeric material from a first crystallinity to a second crystallinity, where the second crystallinity is less than the first crystallinity. In other words, the method can include reducing or decreasing the crystallinity of the polymeric material.

As indicated above, the crystallinity of the polymeric material can be decreased. For example, the crystallinity of the polymeric material, such as UHMWPE, can be decreased to about 50% crystallinity or less (i.e. crystallinity less than 50%). In another example, the crystallinity of the polymeric material can be decreased to within a range of from about 40% crystallinity to about 50% crystallinity. In yet another example, the initial crystallinity of the polymeric material can be decreased by about 5%. In still another example, the initial crystallinity of the polymeric material can be decreased by from about 10% to about 30%.

One way the crystallinity of the polymeric material can be decreased is by heating the polymeric material to a temperature sufficient to decrease its crystallinity. For example, the polymeric material can be heated to about its melt point, or to a temperature above its melt point. Heating the polymeric material in this manner increases the amorphous content of the polymeric material and thus decreases its crystallinity.

After heating the polymeric material to increase its amorphous phase, the polymeric material can be cooled at a rate sufficient to lock in the amorphous phase. For example, the polymeric material can be cooled to a temperature below its melt point to lock in the amorphous phase, and thereby decrease the crystallinity of the polymeric material. The cooling can be accomplished by any method or procedure which results in a cooling rate sufficient to cause an increase in the amorphous phase and thus accomplish a decrease in the crystallinity of the polymeric material. For example, the cooling rate can be in the range of from about 1° C./minute to about 50° C./minute or greater. For example, from about 100° C./minute to about 300° C./minute. The process for cooling the polymeric material can involve any number of cooling media such as liquid nitrogen, alcohol/dry ice, cooled salt water, air, room temperature water, or a cooled surface, such as a metallic surface or a ceramic surface. In addition, cooling gases are also contemplated.

In addition the crystallinity of the polymeric material can be decreased so that a crystallinity gradient is formed in the polymeric material. For example, the polymeric material can be heated to its melt point or to a temperature greater than its melt point and then cooled at a rate sufficient to form a crystallinity gradient in the polymeric material. In one embodiment the crystallinity gradient is positioned such that crystallinity of the polymeric material increases moving in a direction away from the exterior surface of the polymeric material toward an interior location of the polymeric material.

After decreasing the crystallinity of the polymeric material it can be subjected to a crosslinking process. For example, exposing the polymeric material to radiation such as gamma radiation, electron beam, or X-rays will cause the crosslinking of the polymeric material. Such exposure may be in the exemplary range of from about 5 kGy to about 500 kGy, illustratively from about 25 kGy to about 100 kGy, and illustratively from about 30 kGy to about 60 kGy. As indicated above, a specific example of a crosslinked polymeric material that can be utilized in the construction of a device to be implanted in the body of an animal, such as the bearing component described herein, is crosslinked UHM-WPE.

After crosslinking the polymeric material it may be subjected to a post-irradiation free radical quenching process. For example, the free radical containing polymeric material can be melt annealed to quench the free radicals. For example, the free radical containing polymeric material can be placed into a vacuum oven under reduced pressure. To quench substantially all the free radicals present in the polymeric material, the temperature of the vacuum oven can then be raised to above the melting point of the polymeric material (e.g. greater than 135° C.) until it is completely melted. The polymeric material can then be kept at a temperature above its melt point for a time period of about 24 hours, or other time period deemed adequate to quench the free radicals. In any event, the polymeric material subjected to a post-irradiation free radical quenching process will be substantially free of free radicals.

As indicated above, a polymeric material subjected to a treatment described herein can be utilized as a polymeric component of an implantable orthopaedic device, for example a bearing component of a knee, hip, shoulder, or elbow prostheses. Accordingly, the polymeric material can be subjected to a sterilization process, such as being gas plasma sterilized or ethylene oxide sterilized, prior to the orthopaedic device being implanted in the body of an animal. However, it should be appreciated that sterilizing the polymeric material and crosslinking the polymeric material can occur simultaneously.

In another embodiment, the present disclosure provides a method of preparing an implantable orthopaedic device that includes a component made from a polymeric material that is treated by a method described herein. Accordingly, the present disclosure also provides an implantable orthopaedic device that includes a component made from a crosslinked polymeric material, wherein the crosslinked polymeric material has a crystallinity of about 50% or less, or has a crystallinity gradient formed therein. For example, the polymeric material having a crystallinity of about 50% or less, or has a crystallinity gradient formed therein can be crosslinked UHMWPE serving as a bearing component in the orthopaedic device.

Additional features of the present disclosure will become apparent to those skilled in the art upon consideration of the following detailed description of preferred embodiments exemplifying the best mode of carrying out the subject matter of the disclosure as presently perceived.

BRIEF DESCRIPTION OF THE DRAWINGS

FIG. 7 shows percent crystallinity data for the indicated samples; and

DETAILED DESCRIPTION

Figure 1:
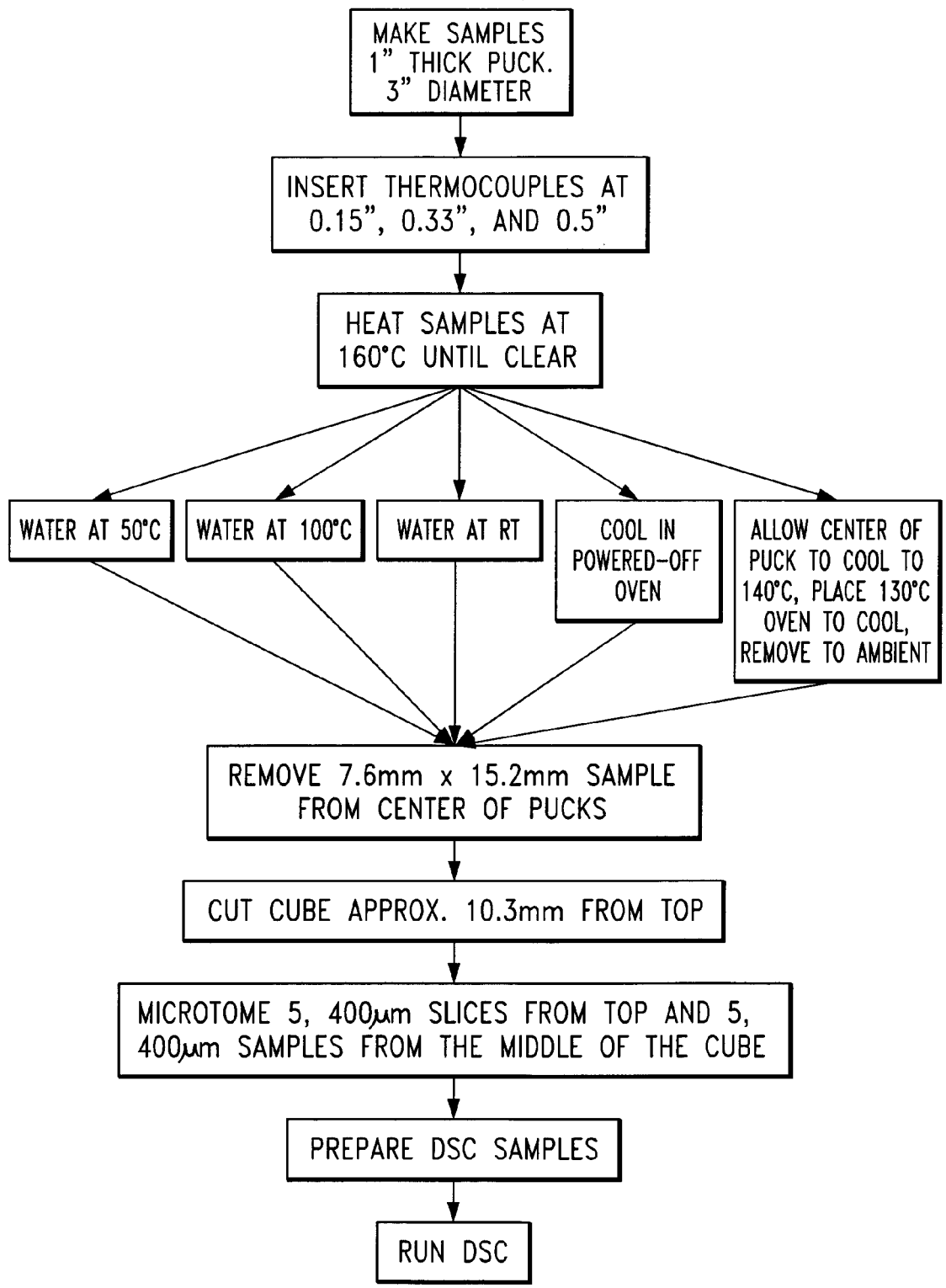
FIG. 1 is a flow chart illustrating an exemplary procedure for decreasing the crystallinity of a polymeric material.

While the invention described herein is susceptible to various modifications and alternative forms, a specific embodiment thereof has been shown by way of example and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

An exemplary embodiment of the present invention is directed to a method for treating a polymeric material for use in an implantable orthopaedic device. As previously mentioned the polymeric material can be consolidated into a work piece if desired. For example, the work piece can be in the form of a rod, bar, sheet or molded component. It should also be appreciated that a porous or nonporous material can be utilized. As indicated the work piece can, for example, be made into a polymeric bearing component of an implantable orthopaedic device. What is meant herein by the term "bearing" is an orthopaedic implant prosthetic bearing of any type, condition, shape, or configuration. Such bearings may be utilized in a number of joint replacement or repair procedures, such as surgical procedures associated with the hip, shoulders, knees, ankles, knuckles, or any other joint. For example, a polymeric material subjected to a treatment of the present disclosure can be utilized as an implantable prosthetic bearing such as a glenoid bearing for implantation into a glenoid of a patient, an acetabular bearing for implantation into an acetabulum of a patient, and a tibial bearing for implantation into a tibia of a patient. Each of the prosthetic bearings include an articulating or bearing surface on which a natural or prosthetic component bears. For example, in the case of the glenoid bearing, a natural or prosthetic humeral head bears on the articulating surface. Similarly, in the case of an acetabular bearing, a natural or prosthetic femoral head bears on the articulating surface. Moreover, in the case of the tibial bearing, one or a pair of natural or prosthetic femoral condyles bear on the articulating surface.

The polymeric material which can be utilized in the present invention can be any medical grade polymeric material which may be implanted into the body of an animal (e.g. the body of a human patient). An example of a polymeric material that can be utilized in the present invention includes for example medical grade polyethylene such as polyethylene homopolymer, high density polyethylene, high molecular weight polyethylene, high density high molecular weight polyethylene, or any other type of polyethylene utilized in the construction of an implant. A more specific example of such a polymer is medical grade ultrahigh molecular weight polyethylene (UHMWPE).

The polymeric material utilized to implant into the body of an animal will have an initial crystallinity. In particular, the polymeric material will have a particular crystallinity prior to being subjected to a method described herein. Various polymeric materials have different degrees of crystallinity. For example, as indicated above, initially the crystallinity of the polymeric material utilized in the present invention can about 50% or greater. In particular, the initial crystallinity of the polymeric material utilized can be, for example, in the range of from about 50% to about 70%. Even more particular, the initial crystallinity of the polymeric material can be, for example, in the range from about 50% to about 60%.

In one embodiment of the invention described herein the initial crystallinity of the polymeric material is changed. In particular, the crystallinity of the polymeric material is decreased as compared to its initial crystallinity. In other words, the crystallinity of the polymeric material is changed from a first crystallinity to a second crystallinity, where the second crystallinity is less than the first crystallinity. In one example the crystallinity of the polymeric material is decreased to about 50% crystallinity or less. For example, the crystallinity of the polymeric material can be decreased to within a range of from about 40% crystallinity to about 50% crystallinity.

In yet another example, the initial crystallinity of the polymeric material can be decreased by about 5%. In still another example, the initial crystallinity of the polymeric material can be decreased by about 10% to about 30%. In a specific example the crystallinity of UHMWPE can be decreased to about 50% or less.

It should be appreciated that the crystallinity of the polymeric material can be decreased in any appropriate manner that does not degrade the physical or chemical characteristics of the material. For example, as previously mentioned, one way the crystallinity of the polymeric material can be decreased is by heating it to a sufficient temperature to increase its amorphous content. For example, the polymeric material can be heated to about its melt point, or to a temperature above its melt point. While there is no intent to be limited to any particular mechanism, heating the polymeric material, e.g. to its melt point, or to a temperature above its melt point, increases the amorphous content of the polymeric material and thus decreases its crystallinity.

After heating the polymeric material to decrease its crystallinity, e.g. increase its amorphous phase, the polymeric material is cooled at a rate sufficient to lock it in a state of reduced crystallinity. For example, the polymeric material can be cooled to a temperature below its melt point to lock in the amorphous phase, and thereby decrease the crystallinity of the polymeric material. The cooling can be accomplished by any method or procedure which results in a cooling rate sufficient to cause an increase in the amorphous phase and thus accomplish a decrease in the crystallinity of the polymeric material. For example, the cooling rate can be in the range from about 1° C./minute to about 50° C./minute. Greater cooling rates are also contemplated. For example, cooling rates from about 100° C./minute to about 300° C./minute or even greater cooling rates can also be utilized. For example, any cooling rate can be utilized as long as the rate is sufficient to "lock" in at least a portion of the increase in the polymeric material's amorphous content, and thus maintain at least some of the decrease in the crystallinity of the polymeric material when returned to a temperature below its melt point.

The process for cooling the polymeric material can involve exposing the material to any number of cooling media such as liquid nitrogen, alcohol/dry ice, a cooled surface as previously mentioned, and cooled salt water. Cooling media may also include, for example, cooling at room temperature or cooling with elevated temperature liquids, gasses, or surfaces, i.e. liquids, gasses, or gasses that have an elevated temperature relative to room temperature, but have a temperature that is cooler than the temperature of the polymeric material being cooled.

After being cooled the polymeric material can be subjected to a crosslinking process. For example, exposing the polymeric material to radiation such as gamma radiation, electron beam, or X-rays causes the crosslinking of the polymeric material. As previously indicated such exposure may be in the exemplary range of from about 5 kGy to about 500 kGy, illustratively from about 25 kGy to about 100 kGy, and illustratively from about 30 kGy to about 60 kGy. As indicated above, a specific example of a crosslinked polymeric material that can be utilized in the construction of a device to be implanted in the body of an animal, such as the bearing component described herein, is crosslinked UHMWPE. For example, after decreasing the crystillinity of the UHMWPE as described above, it can be crosslinked by exposing it to radiation in the range of from about 25 kGy to about 100 kGy.

Once crosslinked, the polymeric material can be subjected to a post-irradiation free radical quenching process. For example, the free radical containing polymeric material can be melt annealed to quench the free radicals. For example, the free radical containing polymeric material can be placed into a vacuum oven under reduced pressure. To quench substantially all the free radicals present in the polymeric material, the temperature of the vacuum oven can then be raised to above the melting point of the polymeric material (e.g. greater than 135° C.) until it is completely melted. The polymeric material can then be kept at a temperature above its melt point for time period of about 24 hours. In any event, the polymeric material subjected to a post-irradiation free radical quenching process will be substantially free of free radicals.

Techniques for crosslinking, quenching, or otherwise preparing, for example, UHMWPE are described in numerous issued U.S. patents, examples of which include U.S. Pat. No. 5,728,748 (and its counterparts) issued to Sun, et al, U.S. Pat. No. 5,879,400 issued to Merrill et al, U.S. Pat. No.

6,017,975 issued to Saum, et al, U.S. Pat. No. 6,242,507 issued to Saum et al, U.S. Pat. No. 6,316,158 issued to Saum et al, U.S. Pat. No. 6,228,900 issued to Shen et al, U.S. Pat. No. 6,245,276 issued to McNulty et al, and U.S. Pat. No. 6,281,264 issued to Salovey et al. The disclosure of each of these U.S. patents is hereby incorporated by reference.

It should be appreciated that a polymeric material subjected to a treatment described herein can be utilized as a polymeric component of an implantable orthopaedic device, for example a bearing component of a knee, hip, shoulder, or elbow prostheses. Accordingly, the polymeric material can be subjected to a sterilization process, such as being gas plasma sterilized, prior to the orthopaedic device being implanted in the body of an animal.

EXAMPLES

Table 1 below lists the conventional steps for producing crosslinked UHMWPE for use in fabricating a device as compared to an example of a process for the crosslinking of a low crystallinity polymeric material for use in device fabrication.

TABLE 1

| Conventional Crosslinked | Low Crystallinity Crosslinked | Low Crystallinity Irradiation Sterilized |
|---|---|---|
| Consolidated UHMWPE (e.g. bar, sheet, machined shape or blank, molded shape, porous shape, etc.) | Consolidated UHMWPE (e.g. bar, sheet, machined shape or blank, molded shape, porous shape, etc.) | Consolidated UHMWPE (e.g. bar, sheet, machined shape or blank, molded shape, porous shape, etc.) |
| | Heated above the melt (e.g. ~135° C.) and cooled below the melt to produce low crystallinity or a crystallinity gradient. | Heated above the melt (e.g. ~135° C.) and cooled below the melt to produce low crystallinity or a crystallinity gradient. |
| Packaged (optional) Irradiated to produce crosslinking | Packaged (optional) Irradiated at lower dose to produce material with about the same wear rate and enhanced mechanical properties or irradiated at the same dose to produce material with lower wear rate and similar mechanical properties. | |

TABLE 1-continued

| Conventional Crosslinked | Low Crystallinity Crosslinked | Low Crystallinity Irradiation Sterilized |
|---|---|---|
| Melt annealed to remove free radicals | Melt annealed to remove free radicals | |
| Components machined | Components machined | Components machined |
| Packaged | Packaged | Vacuum or barrier packaged |
| Gas Plasma or Ethylene Oxide sterilized | Gas Plasma or Ethylene Oxide sterilized | Irradiation sterilized (to produce crosslinking) |

Table 2 below shows the wear rate of disks subjected to a pin on disk wear test. Note that some of the polymeric material was subjected to a cooling procedure as discussed herein and thus have a reduced crystallinity, while others were tested without first decreasing their crystallinity. Note that each material referenced in Tables 2 and 3, i.e. GUR 1020, Hylamer (4150), and GUR 1050, are known examples of UHMWPE. Further note that all crystallinity values cited herein were determined by analyzing about 7.5 mg of the polymeric material with a TA Instruments Differential Scanning Calorimeter (DSC) model 2910 under a nitrogen atmosphere. The DSC method kept the sample of polymeric material isothermally at room temperature for 3 minutes, followed by a ramp to 180° C. at 10° C. per minute, followed by a cool-down cycle to 20° C.

TABLE 2

| Material | Quick Cooling | Starting Crystallinity | Irradiation Dose | Melt Anneal? | Pin-on-Disk Wear Rate (mg/$10^6$ cycles) |
|---|---|---|---|---|---|
| GUR 1020 | None | 56.6% | 60 kGy | Yes | 3.37 |
| GUR 1020 | Liquid Nitrogen | 47.6% | 60 kGy | Yes | 2.00 |
| Hylamer (4150) | None | 69.4% | 60 kGy | Yes | 6.01 |
| Hylamer (4150) | Liquid Nitrogen | 43.9% | 60 kGy | Yes | 1.23 |
| GUR 1050 | None | 51.4% | 60 kGy | Yes | 3.71 |
| GUR 1050 | Liquid Nitrogen | 44.2% | 60 kGy | Yes | NA |

The mechanical properties in Table 3 below indicate a slight loss of tensile strength and yield strength for the quick cooled samples, but no significant loss of elongation or impact strength.

TABLE 3

| Material | Irradiation Dose kGy | Melt Anneal? | Yield Strength ksi | Ultimate Tensile Strength ksi | Percent Elongation | Impact strength kJ/$m^2$ |
|---|---|---|---|---|---|---|
| GUR 1020 as received | 50 | Yes | 2.71 | 7.16 | 369 | 86.2 |
| GUR 1020 quick cool | 50 | Yes | 2.55 | 5.64 | 363 | 83.8 |
| Hylamer (4150) as received | 50 | Yes | 2.87 | 7.32 | 301 | 74.7 |
| Hylamer (4150) quick cool | 50 | Yes | 2.49 | 4.96 | 316 | 72.6 |
| GUR 1050 as received | 50 | Yes | 2.57 | 6.69 | 317 | 75.2 |
| GUR 1050 quick cool | 50 | Yes | 2.42 | 4.99 | 308 | 76.6 |

Figure 8:
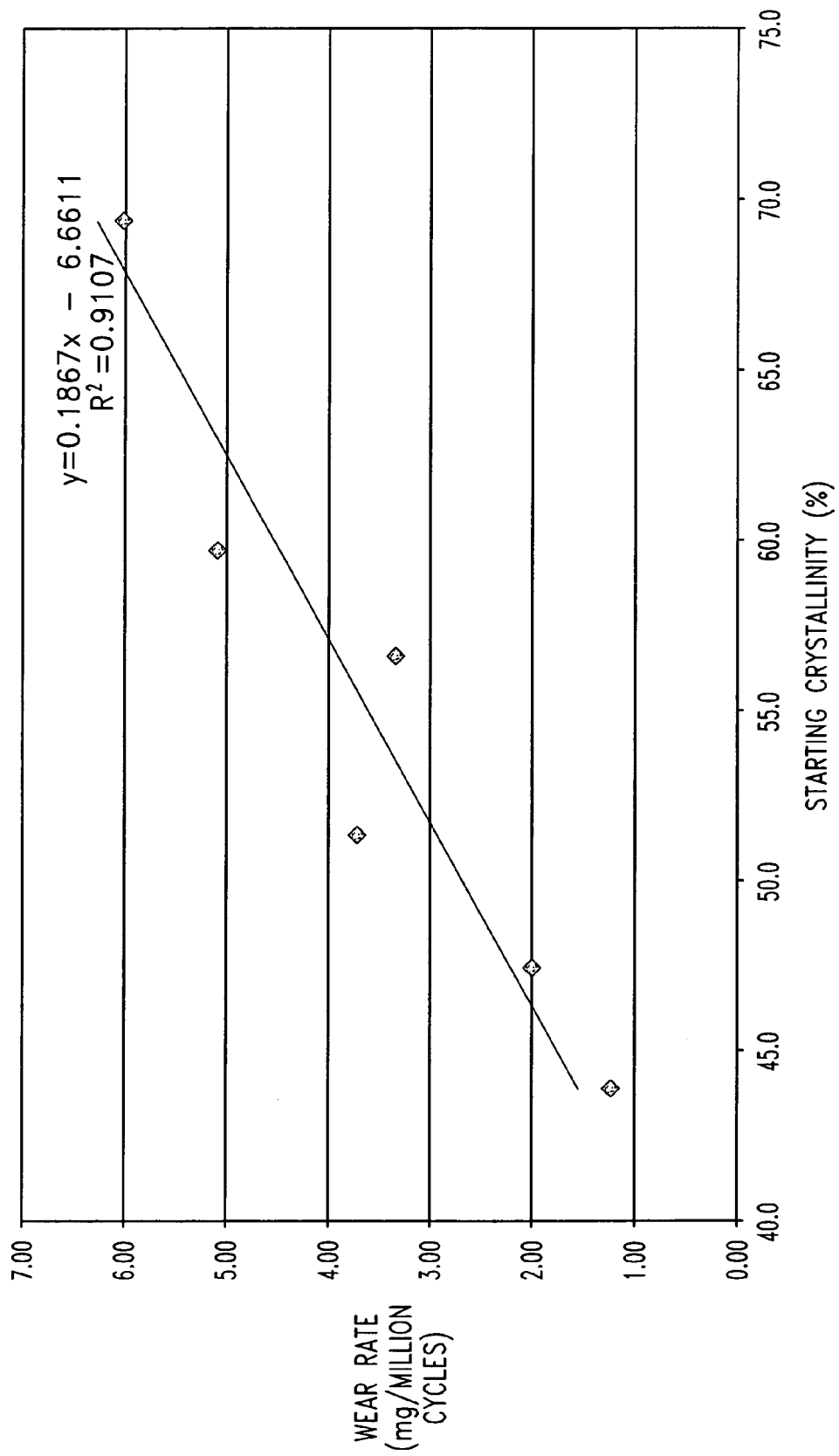
FIG. 8 is a graph illustrating the relationship between wear rate and percent starting crystallinity.

As indicated above, decreasing the crystallinity of the UHMWPE sample prior to it being crosslinked with, for example, 60 kGy of radiation results in a polymeric material having an enhanced wear resistance as compared to a sample that was irradiation crosslinked without first decreasing its crystallinity. This is further illustrated in FIG. 8 which is a graph that depicts the relationship between wear rate and percent starting crystallinity. It should also be appreciated that, as indicated above, decreasing the crystallinity of the UHMWPE sample prior to it being irradiation crosslinked did not adversely affect the other measured mechanical properties to any significant degree.

While not wanting to be limited by any particular theory, it appears that crosslinking is more efficient when the polymeric material is in the amorphous phase as compared to the crystalline phase. Accordingly a lower dose of radiation can be utilized to crosslink this relatively amorphous polymeric material as compared to polymeric material in which the crystalline phase has not been reduced. Since a lower dose of radiation can be utilized to obtain an appropriate degree of crosslinking, the decreased irradiation of the polymeric material will still result in a lower wear rate while not adversely affecting the other mechanical properties of the material. Therefore, the crystallinity reduced polymeric material subjected to a relatively low dose of radiation will have (i) an enhanced wear rate as compared to a polymeric material in which the crystallinity is not reduced prior to being subjected to a relatively low dose of radiation and (ii) enhanced mechanical properties (e.g. properties that are important for the polymeric material to have when it is used in high stress designs) as compared to a polymeric material subjected to a relatively high dose of radiation.

The following examples demonstrate lowering the crystallinity so as to form a crystallinity gradient in a sample of polymeric material. In one embodiment, the crystallinity gradient is formed such that the crystallinity of the polymeric material is relatively low at, or near, an exterior surface of the material, but begins to increase moving in a direction away from the exterior surface of the material and toward the interior or central portion of the material. In other words, the crystallinity of the polymeric material begins to increase moving away from an external surface toward the interior or central portion of the material. Samples of polymeric material having a crystallinity gradient also has the same advantages as discussed above with respect to being able to utilize a relatively low dose of radiation for crosslinking. In addition, polymeric material having a crystallinity gradient have areas that are highly crystalline when irradiated. Accordingly, the mechanical properties in these areas are not adversely affected at all.

In particular, FIG. 1 illustrates a number of procedures which can be utilized to decrease the crystallinity and cool the samples prior to measuring the crystallinity gradient. In particular, pucks of approximately 1-inch thickness were cut from a three inch ram extruded bar of GUR 1050. Using a ⅛" drill bit, 1.5" deep holes were drilled radially from the edge at approximately one sixth, one third, and half the thickness of the puck.

Type T Teflon coated thermocouples from Omega Engineering (part number 5TC-TT-T-24-36) as well as a Type T, ungrounded, stainless steel sheathed thermocouple (part number TMQSS-032-U-6) were used. Using a one ml syringe and an 18-gauge needle, each hole was filled with type Z9 Silicone heat sink compound. The Teflon thermocouples were then wrapped with Teflon tape to increase their exterior diameter. This resulted in a snug fit when they were placed in the pucks. A fourth Teflon coated thermocouple was used externally to monitor the temperature of the cooling medium. For the third test which involved cooling the polymeric material in 100° C. boiling water and the second test which involved cooling the material in 50° C. water, the stainless steel sheathed thermocouple was used in place of the fourth Teflon-coated thermocouple. This was done to prevent the water from causing the thermocouple from shorting out.

For data acquisition, an IBM ThinkPad with a National Instruments DAQcard-6024E was used. LabView software was used for the user interface. Data was recorded at 10 hz using the software. The thermocouples were accurate to +/−five degrees Celsius.

An oven set to 165° C. with a constant flowing stream of Argon at four standard cubic feet per hour was used to heat each puck of polymeric material until it was clear. When the internal thermocouples read within three degrees of the external thermocouple, data logging was initiated and the puck was removed from the oven and placed directly into the cooling medium. As shown FIG. 1, tests were run using the following cooling medium, room temperature water, 50° C. water, 100° C. water, an oven that was powered off, and a series of two ovens. See Table 4 below for a description of the cooling methods used for all tests.

TABLE 4

| Puck ID | Cooling Methods Cooling Method |
|---|---|
| CR-RT | Room temperature Water |
| CR-50 | 50° C. Water |
| CR-50-2 | 50° C. Water |
| CR-100 | 100° C. Water |
| CR-100-2 | 100° C. Water |
| CR-100-3 | 100° C. Water |
| CR-TWO | Cool in air until center was 140° C., then 130° C. oven, then air cool |
| CR-OFF | Oven turned off when part was clear |

Figure 2A:
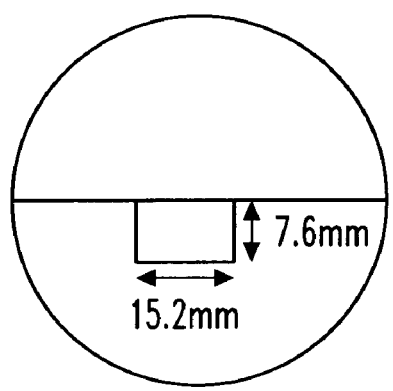
FIG. 2A illustrates how samples were taken for DSC analysis.
Figure 2B:
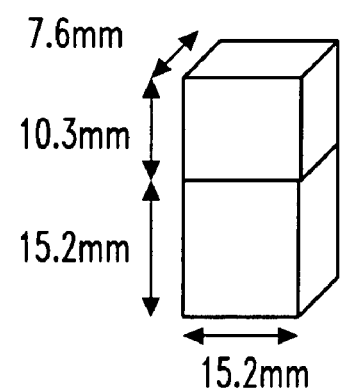
FIG. 2B also illustrates how samples were taken for DSC analysis.

For the samples cooled in water, data acquisition was terminated when the puck reached the temperature of the cooling water. In the case of the puck cooled in the oven, the oven was turned off and the puck was allowed to cool until the internal thermocouples read approximately 120° C. At that point, data acquisition was stopped and the puck was allowed to cool to room temperature in the oven. For the puck cooled in two ovens, the puck was removed from the first oven when clear, then held in the ambient air until the center thermocouple read 140° C., at which point it was placed into the 130° C. oven. The temperature of the 130° C. oven was monitored using a handheld meter and recorded every 5 minutes during the test. When all thermocouples read about 130° C., the part was removed and allowed to cool in the ambient air. Data acquisition was continued until the puck reached approximately 50° C. When all cooling experiments were complete a sample was taken out of the center of each puck measuring 7.6 mm×15.2 mm×the thickness of each puck (see FIG. 2A). The samples were then cut at approximately 15.2 mm from the bottom of the cube, resulting in two pieces, one 7.6 mm×15.2 mm×15.2 mm and one 7.6 mm×15.2 mm×10.3 mm (see FIG. 2B). From the 10.3 mm thick cube, five 400 μm slices were microtomed from the original surface of the puck. From the 15.2 mm cube, ten 400 μm slices were taken from the cut edge (representing the middle of the puck), with the first five being discarded, keeping the slices at approximately 12700 μm, 12300 μm, 11900 μm, 11500 μm, and 11100 μm (depth to the center of the 400 μm slice). The first three slices from each piece (200 μm, 600 μm, 1000 μm and 12700 μm, 12300 μm, 11900 μm) were then used for testing. From each slice, two, 5 mm punches were taken for DSC analysis for a total of six samples from the surface and six samples from the center of each puck. For samples CR-100-3 and CR-TWO, the slices taken at 11500 μm and 11100 μm were used to complete the data.

Cooling rates were calculated for each thermocouple by dividing the temperature change through the interval 140-130° C. by the time it took each thermocouple to pass through that range. This range was selected in order to determine the cooling rate at or slightly above the melt point, and definitely through the melt point. In order to pick the times for each thermocouple, time-temperature graphs were enlarged around the temperature range of 128-142° C. using Excel. Then, using the mouse, points were selected in the approximate middle of each temperature band at 140° C. and 130° C. and the time was read off. Cooling rate calculations are shown below in Table 5.

TABLE 5

Cooling Rate Calculations

| Approximate Thermocouple Depth (mm) | Transition Time 140-130° C. (sec) | Cooling Rate (° C./min) |
|---|---|---|
| CR-1-N | | |
| 3.8 | 12.8 | 47.1 |
| 9.7 | 15.5 | 38.7 |
| 12.7 | 14.3 | 42.0 |
| CR-RT | | |
| External | 2.60 | 231 |
| 4.0 | 33.6 | 17.9 |
| 9.8 | 70.5 | 8.51 |
| 13.5 | 72.1 | 8.32 |
| CR-50 | | |
| External | 2.60 | 231 |
| 4.2 | 16.00 | 37.5 |
| 8.7 | 78.6 | 7.63 |
| 13.6 | 84.8 | 7.08 |
| CR-50-2 | | |
| External | 3.20 | 188 |
| 4.4 | 31.3 | 19.2 |
| 8.9 | 89.7 | 6.69 |
| 13.3 | 127 | 4.71 |
| CR-100-3 | | |
| External | 1.70 | 353 |
| 4.2 | 38.7 | 15.5 |
| 8.6 | 138 | 4.34 |
| 12.9 | 194 | 3.09 |
| CR-TWO | | |
| External | 1.70 | 353 |
| 4.4 | 655 | 0.92 |
| 8.9 | 464 | 1.29 |
| 13.3 | 607 | 0.99 |
| CR-OFF | | |
| External | 1263 | 0.48 |
| 4.6 | 1258 | 0.48 |
| 7.8 | 1138 | 0.53 |
| 13.3 | 1223 | 0.49 |

Figure 3:
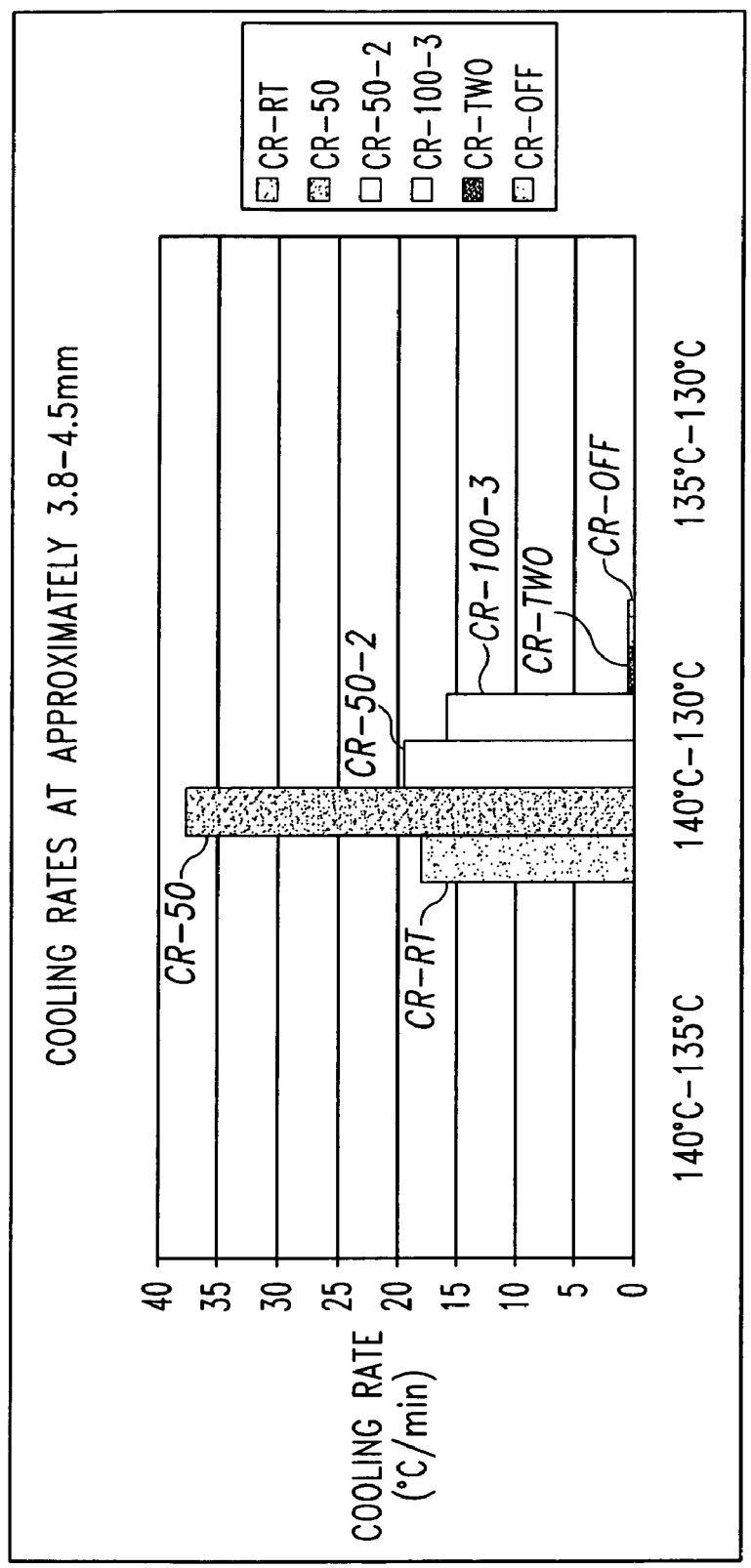
FIG. 3 illustrates the cooling rates for the 3.8-4.5 mm thermocouple.
Figure 4:
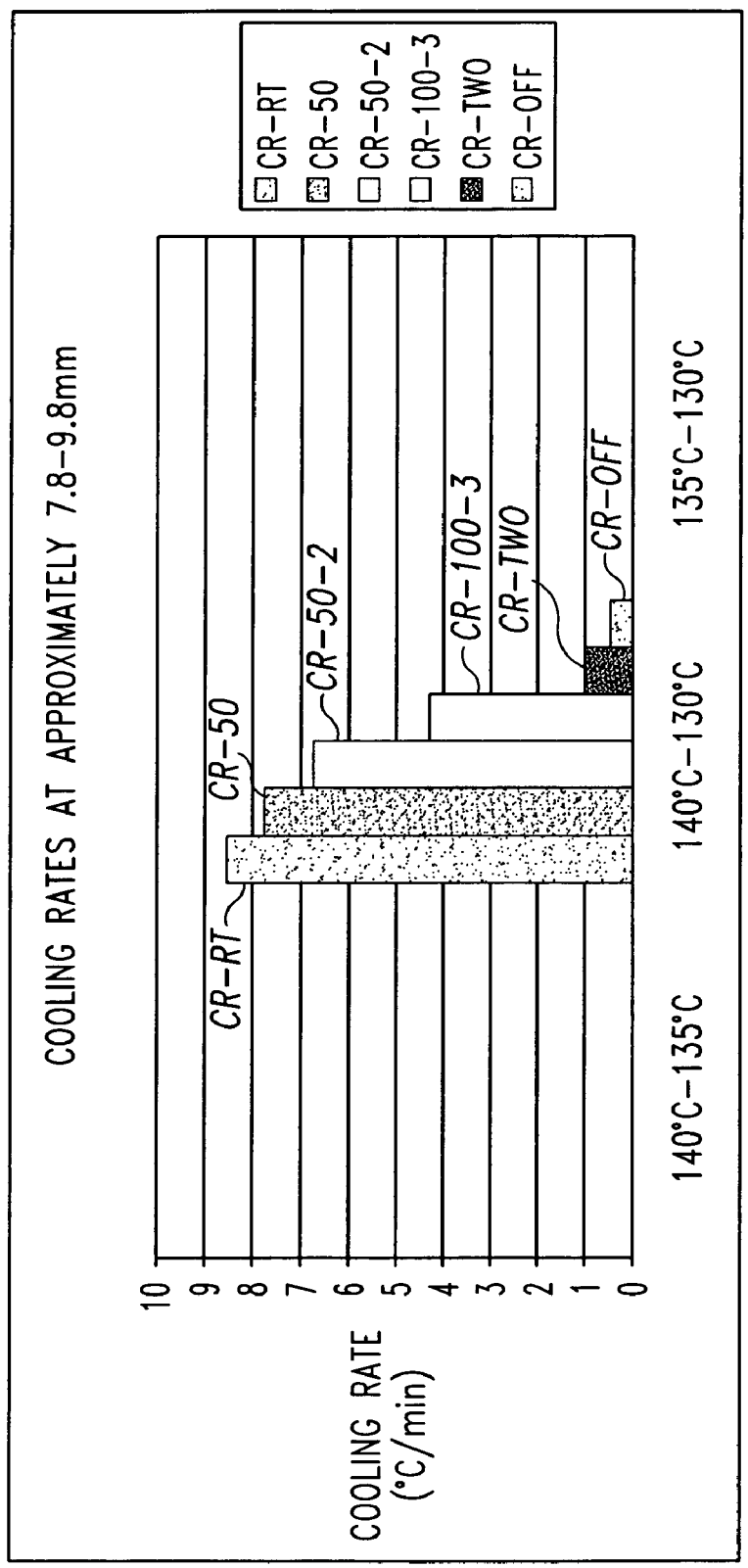
FIG. 4 illustrates the cooling rates for the 7.8-9.8 mm thermocouple.
Figure 5:
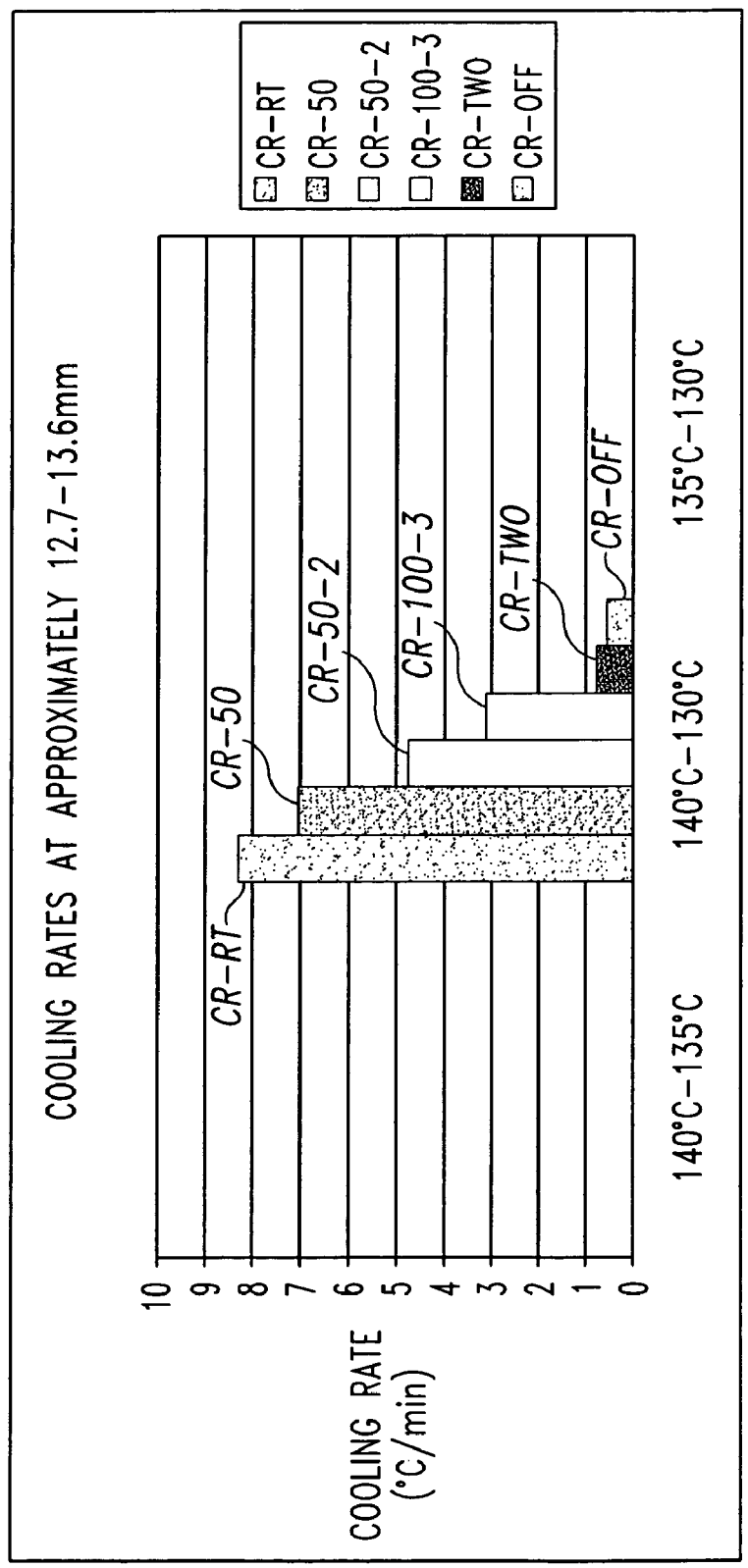
FIG. 5 illustrates the cooling rates for the 12.7-13.6 mm thermocouple.

For comparison, the cooling rate for liquid nitrogen quenching is also included in Table 5 (CR-1-N). A comparison of cooling rates for the outermost thermocouple (3.8-4.5 mm), the second thermocouple (7.8-9.8 mm) and the center thermocouple (12.7-13.6 mm) are shown in FIGS. 3-5. Note that a second puck was cooled in 50° C. water. The cooling rate calculations for the second puck (CR-50-2) can be seen in Table 5.

The crystallinity data from each group can be found in FIG. 7. A crystallinity difference from the surface to the center is seen in each of the samples demonstrating the formation of a crystallinity gradient in each puck. The greatest crystallinity difference from the surface to the center of the puck was seen in the puck cooled in boiling water (CR-100). The smallest crystallinity difference from the surface to the center of the puck was seen in the puck that was allowed to cool in the oven that was turned off when the puck turned clear (CR-OFF).

Figure 6:
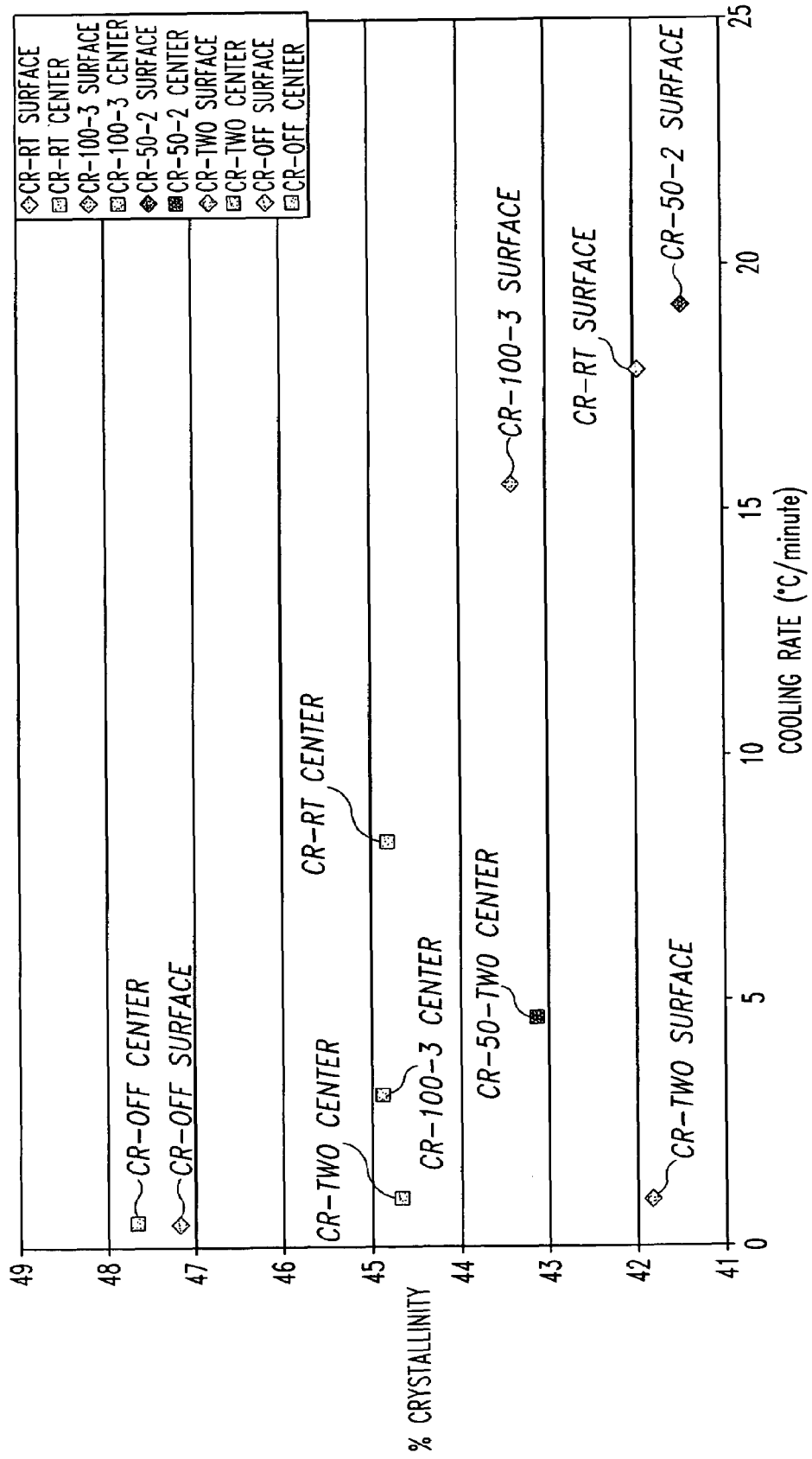
FIG. 6 depicts percent crystallinity as a function of cooling rate.

FIG. 6 shows percent crystallinity as a function of cooling rate. In FIG. 6 the percent crystallinity from the middle was plotted against the thermocouple in the middle of the puck, the crystallinity from near the surface was plotted against the cooling rate for the 3.8-4.5 mm thermocouple, which would be cooling slower than the surface. This is the probable explanation for the low crystallinity at the surface of the CR-TWO surface sample which probably crystallized in air before the puck was placed in the 130° C. oven, yet it is plotted against a much slower cooling rate about 4.4 mm from the surface of the puck. FIG. 6 shows that there is a trend for most samples with higher cooling rates producing lower crystallinities.

Another observation is that it appears the surface of the puck crystallizes rapidly in the few seconds it takes to remove it from the oven and place it in the cooling media. In several tests (CR-RT, CR-50, CR-100) the crystallinity values for the samples taken from 200μ and 600 μm were similar in value, while the crystallinity value at 1000 μm was higher. Note that while care was taken to keep the puck in the ambient air as short of a time as possible, it appears that the crystallinity near the surface may have been established during the transition between the oven and the cooling media.

It is clear that utilizing a warmer cooling medium (e.g. warm water and hot water) resulted in the formation of a crystallinity gradient. However, it should be appreciated that a cold medium, such as liquid nitrogen, can also result in the formation of a crystallinity gradient. While there is no intent to be limited to any particular mechanism, it appears that the low thermal conductivity of polymeric materials, such as UHMWPE, produces a cooling gradient during the cooling process, which in turn also produces a crystallinity gradient in the material as discussed above. It should also be appreciated that the quicker one cools the polymeric material the greater the thickness of the low crystallinity region as measured from an exterior surface of the polymeric material to its interior or central portion. In other words, the quicker the polymeric material is cooled, the greater the proportion of the material is locked into the amorphous phase as opposed to the crystalline phase.

A polymeric material having a crystallinity gradient as described above can be subjected to a crosslinking process as previously discussed. In particular, the polymeric material having a crystallinity gradient can be crosslinked by exposing it to a medium or low dose of radiation. As discussed above, exposing the polymeric material having a crystallinity gradient to a medium or low dose of radiation results in the material having an enhanced wear rate while not adversely affecting the other mechanical properties of the material. In particular, subjecting a polymeric material having a crystallinity gradient to a medium or low dose of radiation will result in the material having (i) a lower wear rate as compared to a polymeric material in which the crystallinity is not reduced prior to being subjected to a relatively low dose of radiation, (ii) enhanced mechanical properties (e.g. properties that are important for the polymeric material to have when it is used in high stress designs) as compared to a polymeric material subjected to a relatively high dose of radiation, and (iii) the high crystallinity areas of the polymeric material have enhanced mechanical properties as compared to low crystallinity areas of the gradient.

As indicated above, the polymeric material having its crystallinity reduced, e.g. in the form of a crystallinity gradient, can be utilized as a component of an implantable orthopaedic device, for example a bearing component of a knee, hip, shoulder, or elbow prostheses. For example, the wear surface of the component having a relatively low crystallinity while the locking features (e.g. tabs) having a high crystallinity.

While the disclosure has been illustrated and described in detail in the foregoing description, such illustration and description is to be considered as exemplary and not restrictive in character, it being understood that only the preferred embodiments have been shown and described and that all changes and modifications that come within the spirit of the disclosure are desired to be protected.

The invention claimed is:

1. An implantable orthopaedic device, comprising:
a component made from a polymeric material, wherein the polymeric material has a crystallinity gradient formed therein and the crystallinity gradient is positioned such that the crystallinity of the polymeric material increases moving in a direction away from an exterior surface of the polymeric material toward an interior of the polymeric material.

2. The device of claim 1, wherein:
polymeric material includes crosslinked UHMWPE.

3. An implantable orthopaedic device, comprising:
a bearing component which includes crosslinked UHMWPE, wherein the crosslinked UHMWPE has a crystallinity gradient formed therein and the crystallinity gradient is positioned such that crystallinity of the polymeric material increases moving in a direction away from an exterior surface of the polymeric material toward an interior of the polymeric material.

4. A method of preparing an implantable orthopaedic device that includes a component made from a polymeric material, the method comprising:
heating the polymeric material to a temperature sufficient to cause a decrease in the crystallinity of the polymeric material;
cooling the polymeric material at a rate sufficient to maintain at least a portion of the decrease in the crystallinity of the polymeric material; and
crosslinking the polymeric material after being cooled.

5. The method of claim 4, wherein:
the crystallinity of the polymeric material is decreased by about 5% or more as compared to an initial crystallinity of the polymeric material prior to being heated.

6. The method of claim 4, wherein:
the crystallinity of the polymeric material is decreased by about 10% or more as compared to an initial crystallinity of the polymeric material prior to being heated.

7. The method of claim 4, wherein:
the crystallinity of the polymeric material being crosslinked is less than about 50%.

8. The method of claim 4, wherein:
decreasing the crystallinity includes heating the polymeric material to its melt point or to a temperature greater than its melt point.

9. The method of claim 4, further comprising:
quenching free radicals present in the polymeric material subsequent to the crosslinking.

10. The method of claim 4, further comprising:
sterilizing the polymeric material.

11. The method of claim 10, wherein:
sterilizing the polymeric material and crosslinking the polymeric material occur simultaneously.

12. The method of claim 4, wherein:
cooling the polymeric material includes forming a crystallinity gradient in the polymeric material.

13. The method of claim 4, wherein:
crosslinking the polymeric material includes subjecting the polymeric material to radiation in the range of from about 25 kGy to about 100 kGy.

* * * * *